United States Patent [19]

Tamura et al.

[11] Patent Number: 5,488,137

[45] Date of Patent: Jan. 30, 1996

[54] ACRYLIC ACID ESTER DERIVATIVE HAVING A TRIPHENYL AMINE SKELETON

[75] Inventors: Hiroshi Tamura, Susono; Toshio Fukagai; Naoshi Mishima, both of Numazu; Masaomi Sasaki, Susono, all of Japan

[73] Assignee: Ricoh Company, Ltd., Tokyo, Japan

[21] Appl. No.: 215,606

[22] Filed: Mar. 22, 1994

Related U.S. Application Data

[62] Division of Ser. No. 912,200, Jul. 13, 1992, Pat. No. 5,322,753.

[30] Foreign Application Priority Data

Jul. 12, 1991 [JP] Japan .................................. 3-198898

[51] Int. Cl.[6] .................................. C07C 69/533
[52] U.S. Cl. .................. 560/141; 560/140; 560/142; 560/221
[58] Field of Search .................. 560/138, 142, 560/141, 221, 223, 140

[56] References Cited

U.S. PATENT DOCUMENTS 3,567,450  3/1971  Brantly .

5,153,087  10/1992  Tamura et al. .

*Primary Examiner*—Christopher Henderson
*Attorney, Agent, or Firm*—Oblon, Spivak, McClelland, Maier, & Neustadt

[57] ABSTRACT

An electrophotographic photoconductor is composed of a substrate and a photoconductive layer formed thereon. The photoconductive layer is composed of a polymer including an acrylic acid ester moiety of formula (I) as repeat unit:

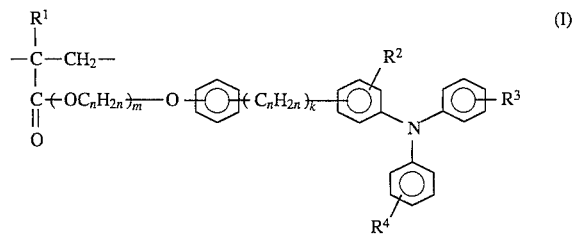

wherein $R^1$ represents hydrogen or a methyl group; $R^2$, $R^3$, and $R^4$ each represent an alkyl group having 1 to 4 carbon atoms, a benzyl group, a phenyl group, a phenoxyl group, chlorine or bromine; n is an integer of 1 to 4; m is 0 or 1; and k is 0 or 1.

The polymer and the monomer from which the polymer is prepared are synthesized.

2 Claims, 4 Drawing Sheets

FIG. I

ACRYLIC ACID ESTER DERIVATIVE HAVING A TRIPHENYL AMINE SKELETON

This is a division of application Ser. No. 07/912,200, filed on Jul. 13, 1992 now U.S. Pat. No. 5,322,753, granted Jun. 21, 1994.

BACKGROUND OF THE INVENTION

1. Field of the Invention

The present invention relates to a novel acrylic acid ester derivative having a triphenylamine skeleton, a polymer comprising such an acrylic acid ester moiety as repeat unit, and an electrophotographic photoconductor comprising a substrate and a photoconductive layer formed thereon, which comprises the above polymer.

2. Discussion of Background

Recently, organic photoconductors (OPC) are widely used in copying machines and printers. Such organic photoconductors comprise, for example, a substrate and a photoconductive layer. The photoconductive layer may comprise a charge generation layer (CGL) and a charge transport layer (CTL) which are successively overlaid on the substrate. The CTL is in the form of a film which comprises a low-molecular-weight charge transporting material (CTM) dispersed in a binder resin in a certain concentration. The addition of the CTM to the binder resin causes deterioration of the mechanical strength of the binder resin itself. The CTL is fragile and has a low tensile strength. It is considered that the above-mentioned deterioration of the mechanical strength of the binder resin causes some problems in the photoconductor, such as wear, flaw, peeling, and crack.

There have been proposed many photoconductive in which a high-molecular-weight material such as polyvinyl anthracene or polyvinyl pyrene is singly used as a charge transporting material in the CTL. However, these photoconductors comprising the above-mentioned high-molecular-weight charge transmitting material do not have sufficient mechanical strength or electrical characteristics.

A photoconductor comprising an acrylic polymer in the CTL is described by M. Stolka in J. POLYM. SCI. VOL. 21, 969. When this acrylic polymer is employed in the CTL, the charge mobility is so low that a sufficiently high photosensitivity for use in practice cannot be obtained.

Furthermore, a photoconductor in which a vinyl polymer of hydrazone is used in the CTL is disclosed in '89 JAPAN HARD COPY p. 67. This photoconductor has a relatively high residual potential.

Photoconductors comprising carbazole polymers described in Japanese Laid-Open Patent Applications 1-115915, 1-141902, and 1-141939 have low photosensitivities. Although the photoconductors described in Japanese Laid-Open Patent Applications 1-134456, 1-134457, and 1-134462 have good photosensitivity, they have problems in the residual potential and in the changes in the photosensitivity. In addition, the compounds described in Japanese Laid-Open Patent Application 64-9964 cannot be easily synthesized, and therefore are not suitable for use in practice.

SUMMARY OF THE INVENTION

Accordingly, a first object of the present invention is to provide an electrophotographic photoconductor having high photosensitivity and durability.

A second object of the present invention is to provide a novel acrylic acid ester derivative having a triphenylamine skeleton.

A third object of the present invention is to provide a novel polymer comprising an acrylic acid ester moiety as repeat unit, which polymer is used as a charge transporting material in the electrophotographic photoconductor.

The first object of the present invention can be achieved by an electrophotographic photoconductor comprising a substrate by an photoconductive layer formed thereon, which comprises a polymer comprising an acrylic acid ester moiety of formula (I) as repeat unit:

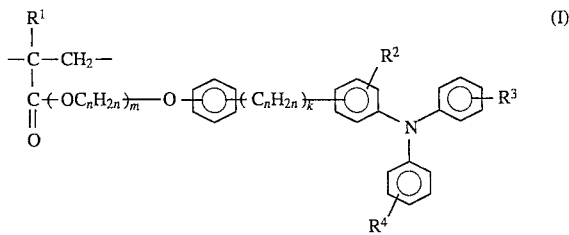

wherein $R^1$ represents hydrogen or a methyl group; $R^2$, $R^3$, and $R^4$ each represent an alkyl group having 1 to 4 carbon atoms, a benzyl group, a phenyl group, a phenoxyl group, chlorine, or bromine; n is an integer of 1 to 4; m is 0 or 1; and k is 0 or 1.

The second object of the present invention can be achieved by an acrylic acid ester having formula (II):

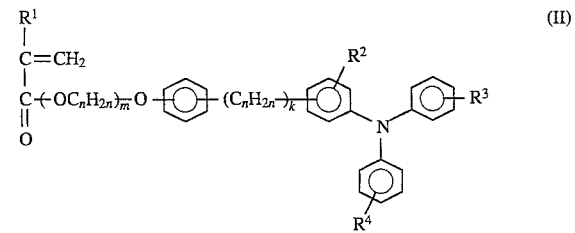

wherein $R^1$, $R^2$, $R^3$, $R^4$, n, m and k are respectively the same as in formula (I).

The third object of the present invention can be achieved by the previously mentioned polymer comprising an acrylic acid ester moiety of formula (I) as repeat unit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
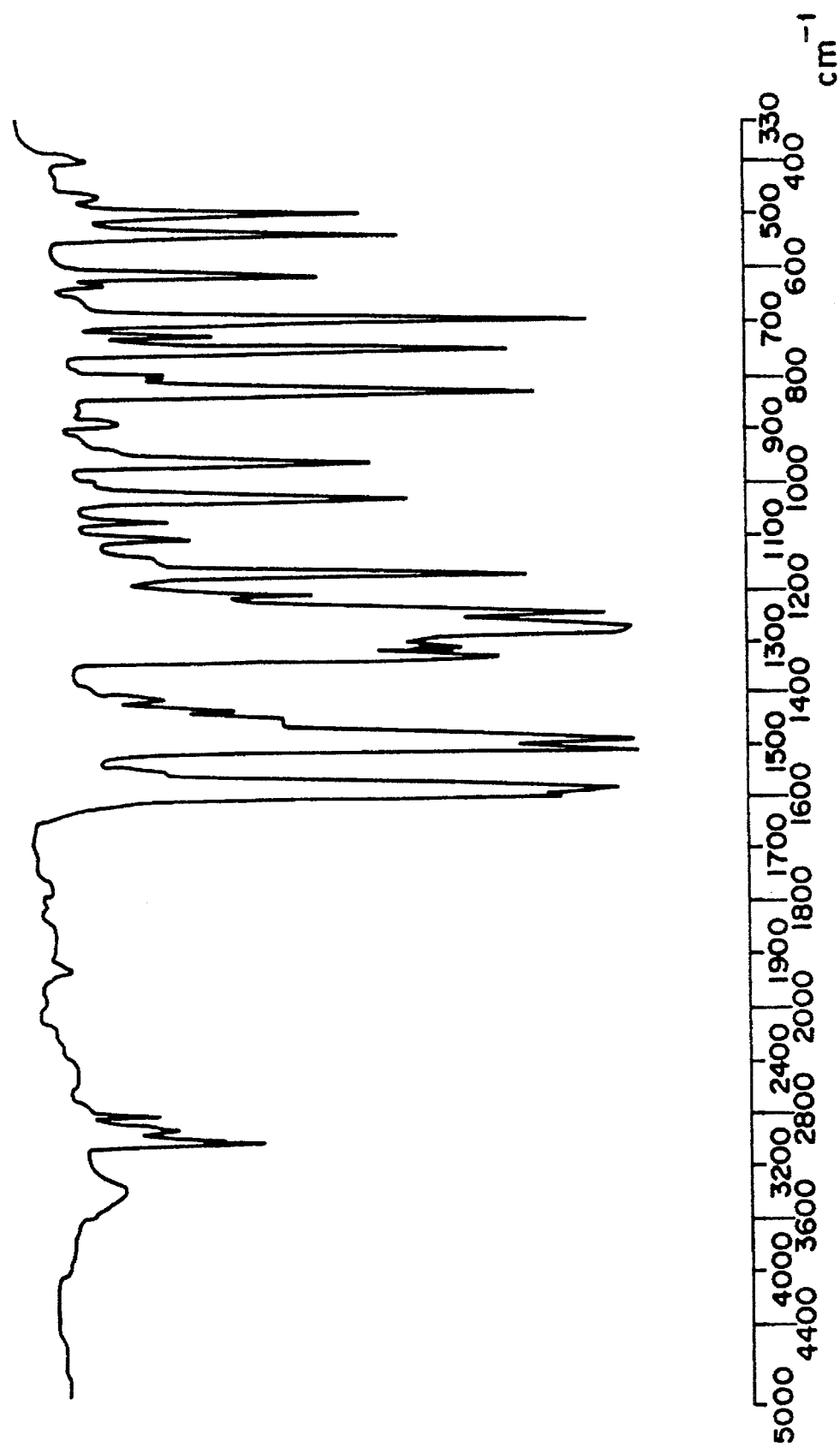
FIG. 1 is an IR spectrum of 4-diphenylamino-4'-methoxystilbene.

An acrylic acid ester having formula (II-1) of the present invention can be synthesized in accordance with the reaction scheme as shown below:

[Reaction Scheme]

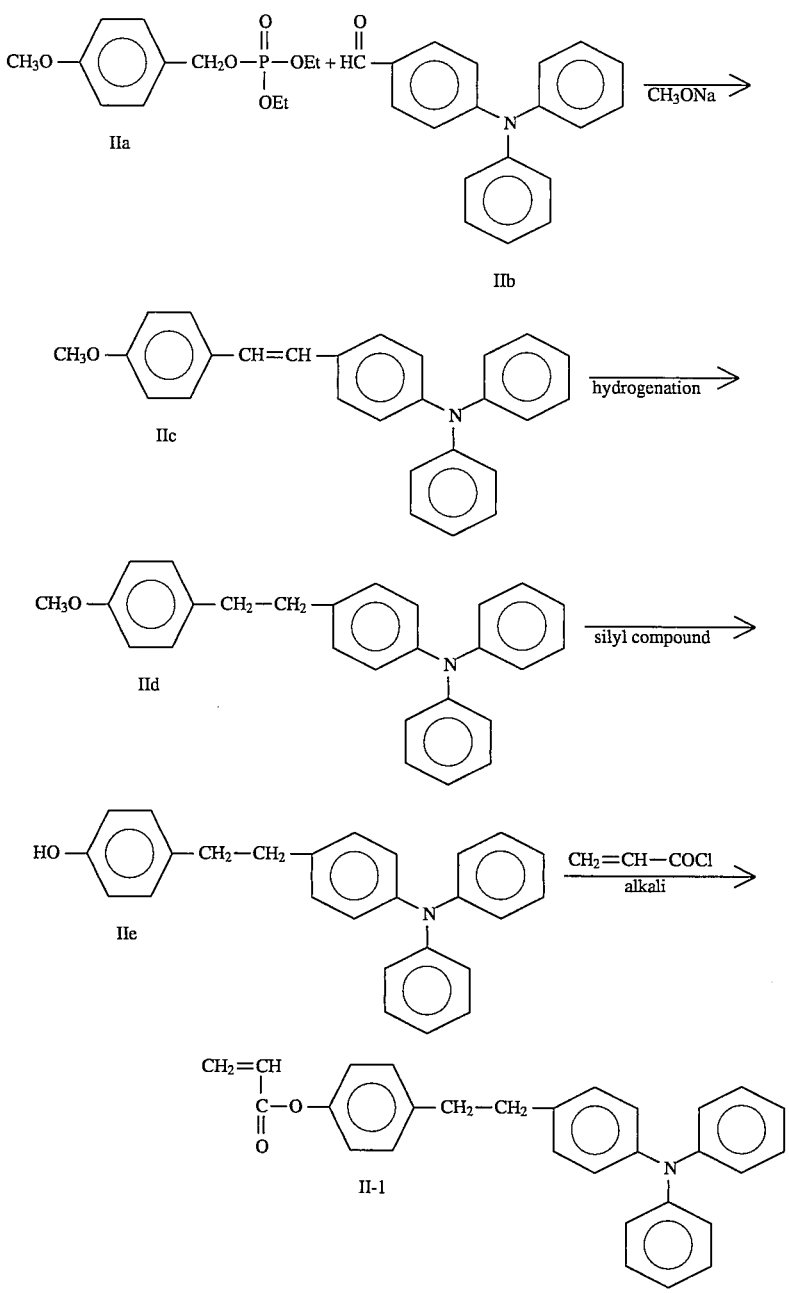

As can be seen from the reaction scheme, 4-(N,N-diphenylamino)benzaldehyde (IIa) is allowed to react with diethylmethoxybenzyl phosphonate (IIb) in the presence of sodium methylate to synthesize 4-diphenylamino-4'-methoxystilbene (IIc). The thus obtained compound (IId) is hydrogenated and is then subjected to hydrolysis using a silyl compound, so that the methoxy group in the compound is converted to —OH. The thus obtained compound (IIe) is allowed to react with acryl chloride in the presence of an alkali, whereby the acrylic acid ester having formula (II-1) of the present invention can be synthesized.

In the above process of synthesizing the acrylic acid ester of the present invention, the compound (IIe) may be allowed to react with epichlorohydrin instead of acryl chloride in the presence of an alkali after hydrolysis, so that an alkyleneoxy chain in the acrylic acid ester thus obtained can be elongated.

Furthermore, a polymer comprising an acrylic acid ester moiety of formula (I) as repeat unit can be obtained by polymerizing a monomer of the acrylic acid ester of formula (II) which is dissolved in a solvent such as toluene, in the presence of a peroxide or an azo-type initiator.

It is preferable that the molecular weight of the polymer of the present invention which comprises the acrylic acid ester moiety as repeat unit be 8,000 to 200,000.

Specific examples of the above-mentioned polymer of the present invention are as follows in which only the repeat units are shown for simplicity:

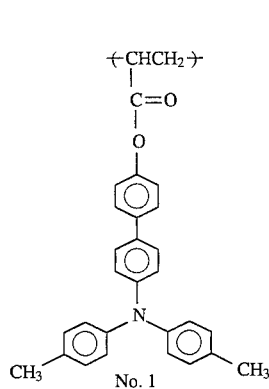
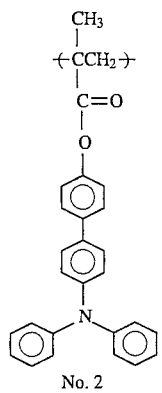
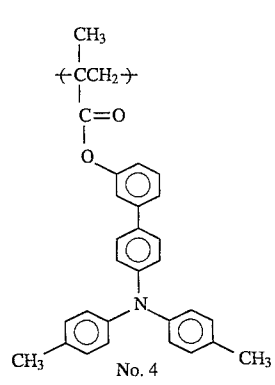
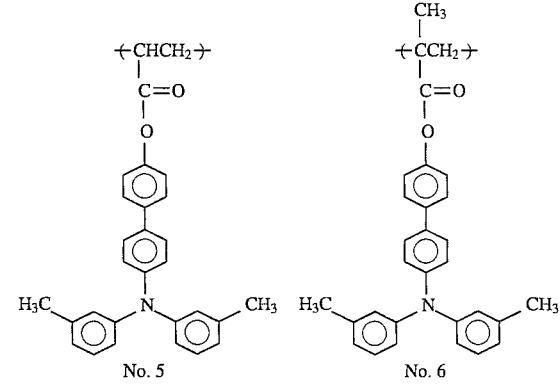
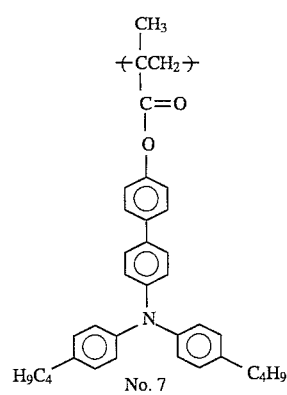
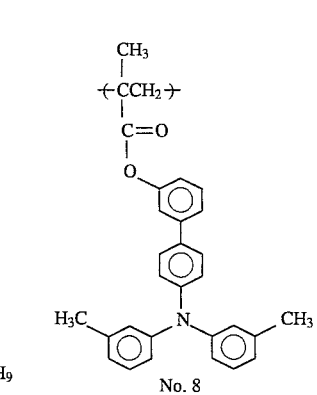
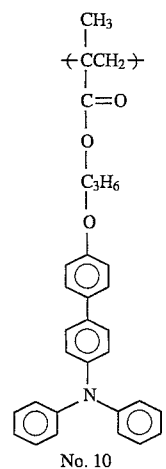
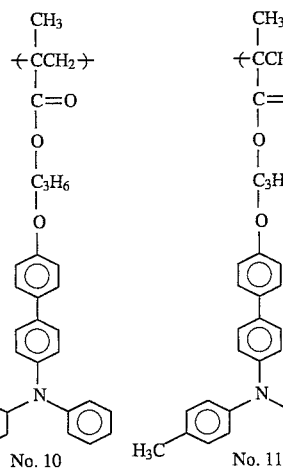
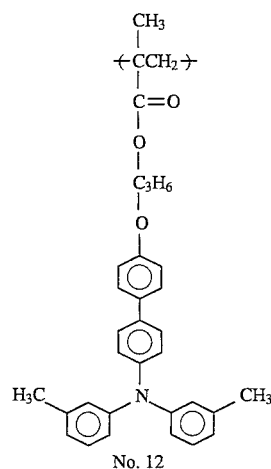
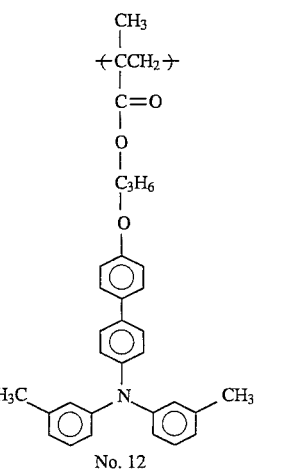

-continued
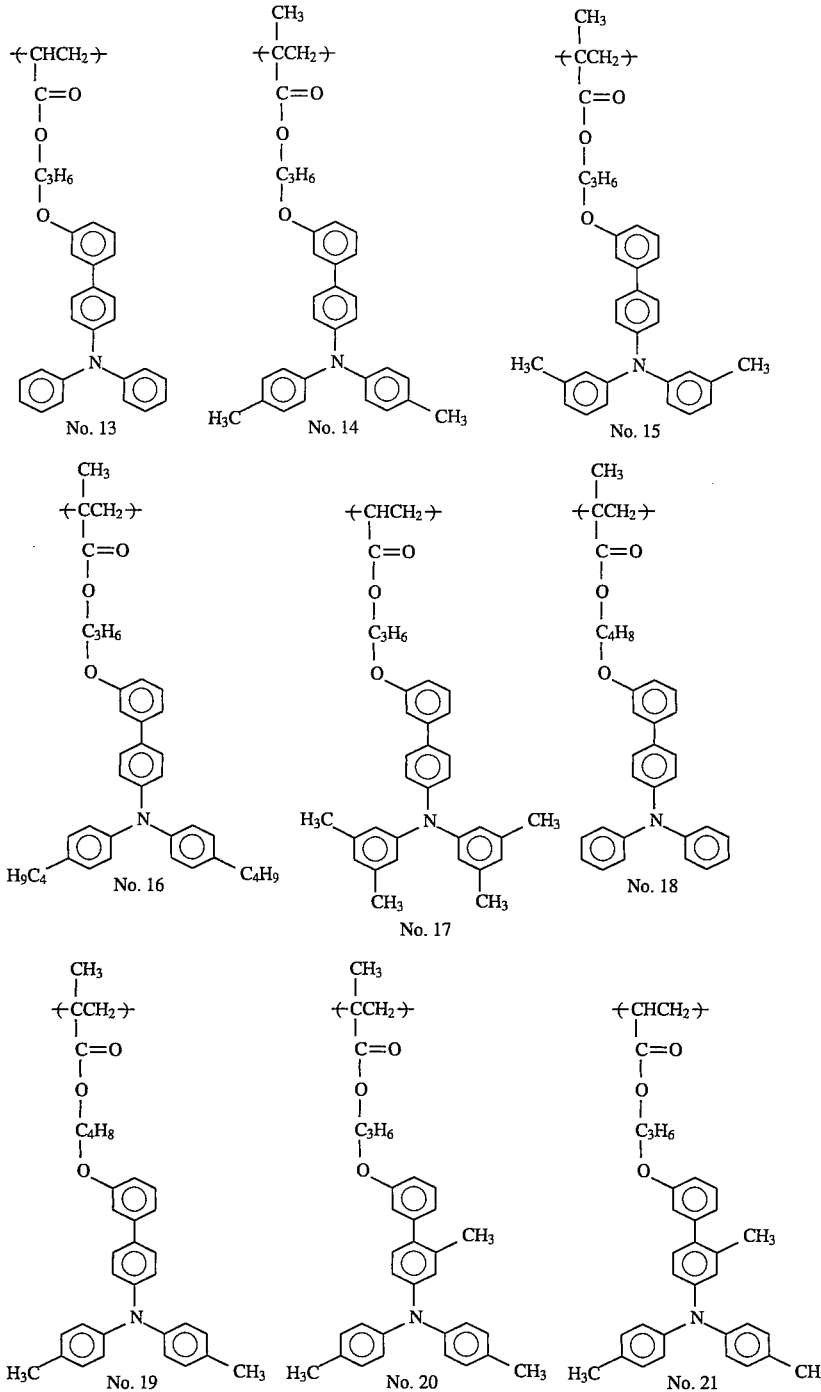

-continued
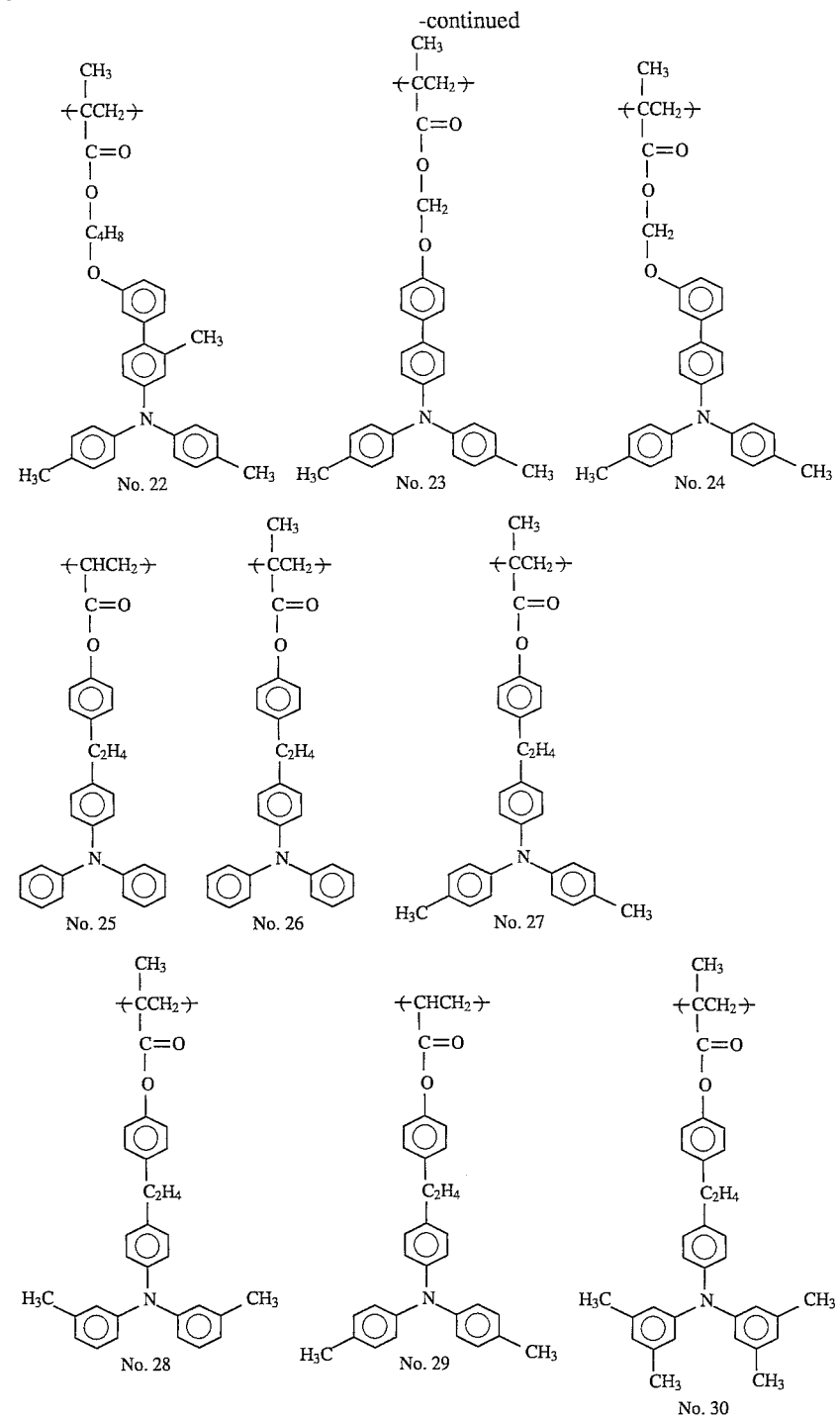

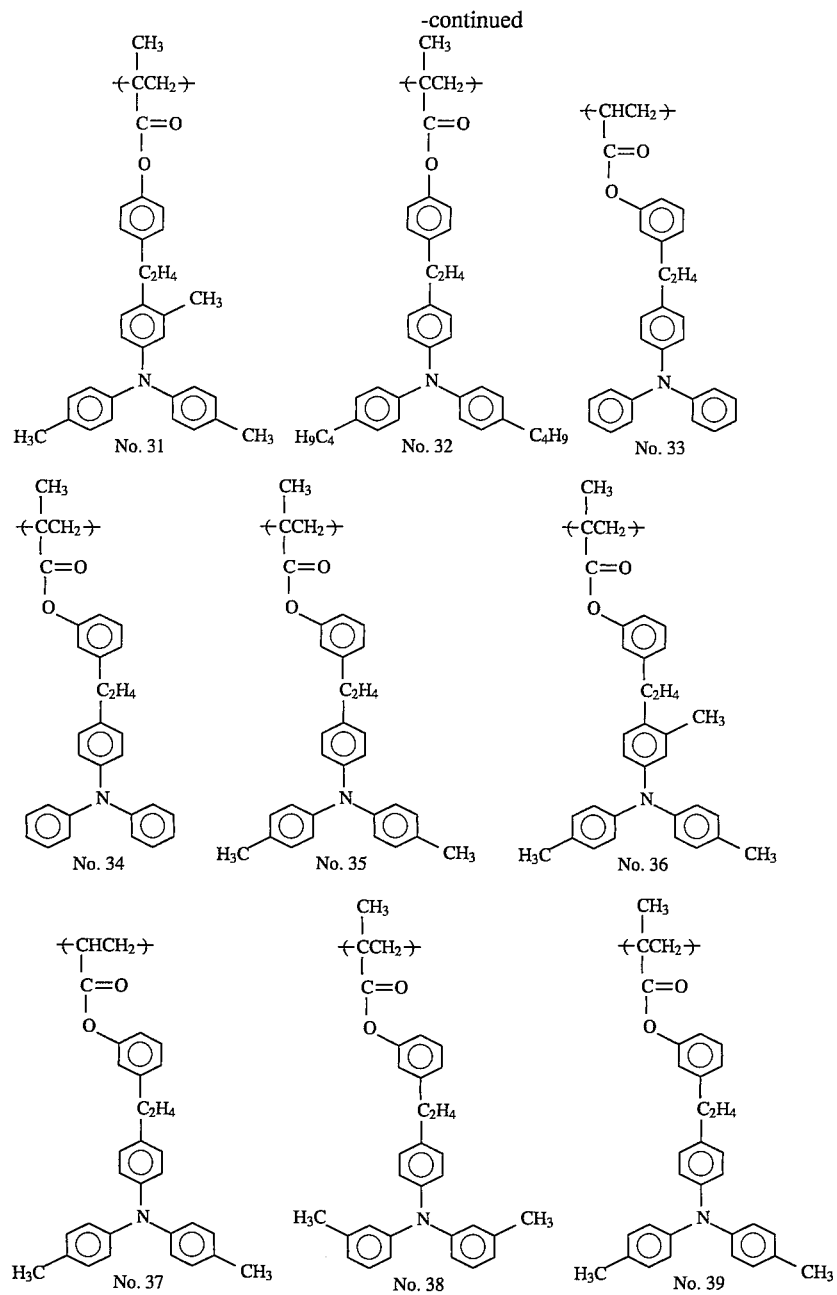

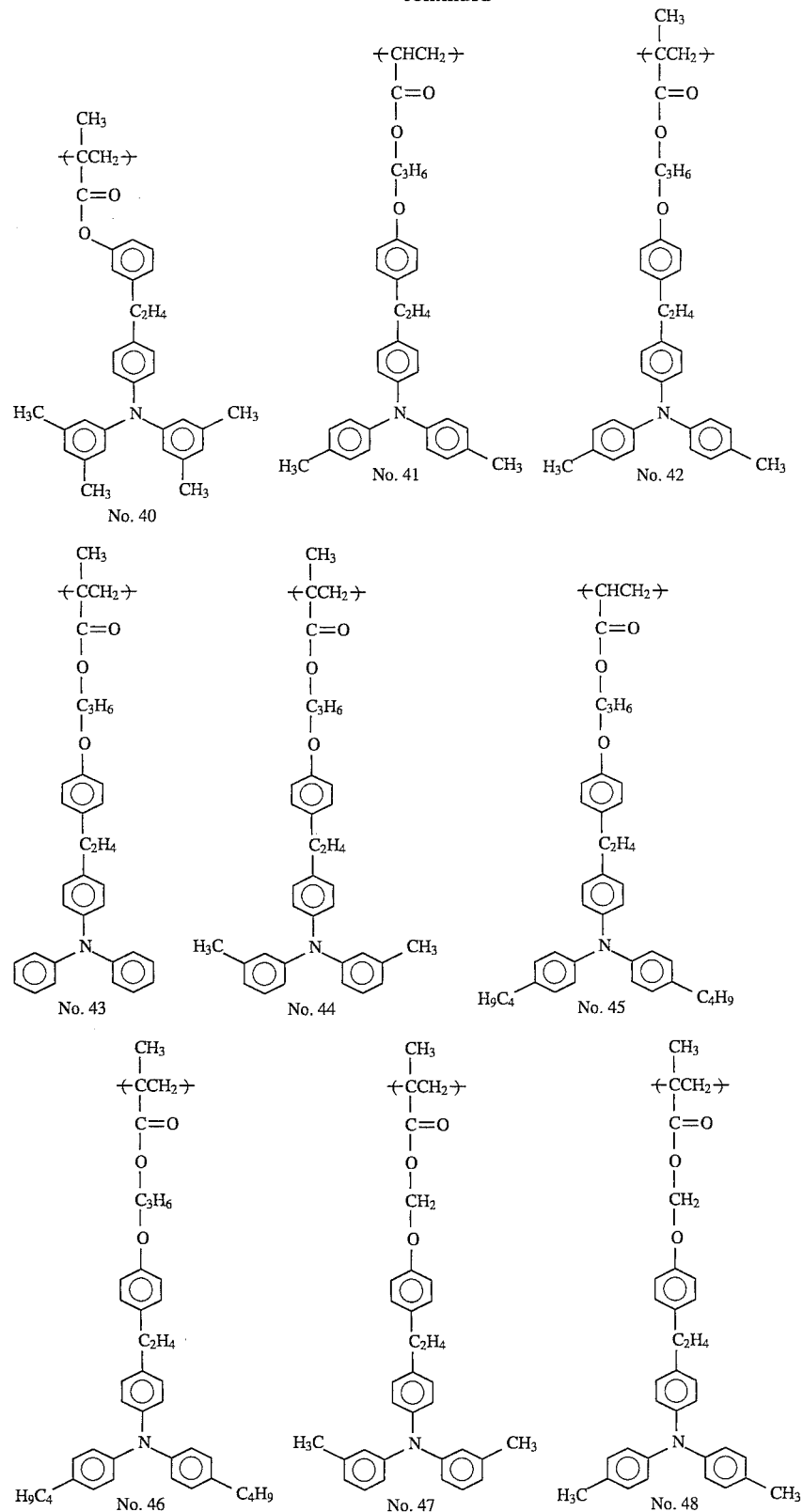

-continued
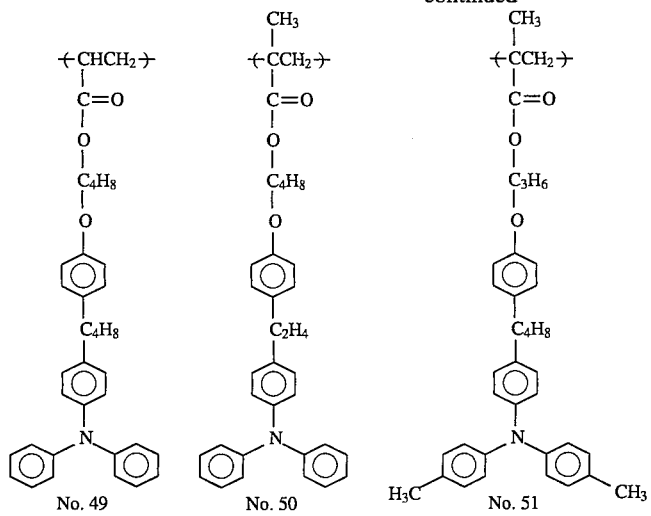
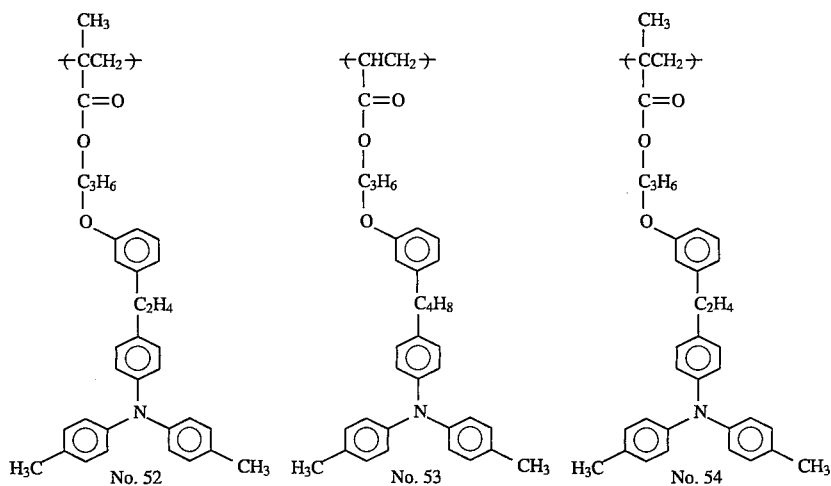
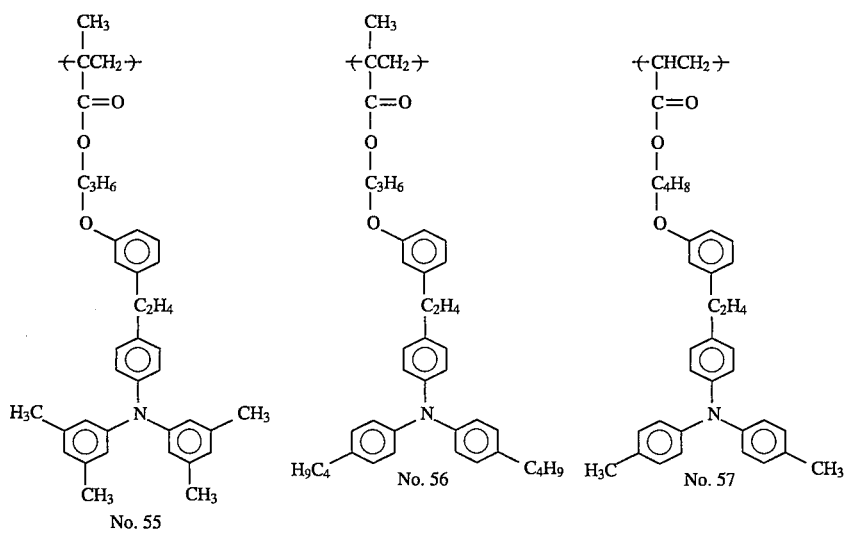

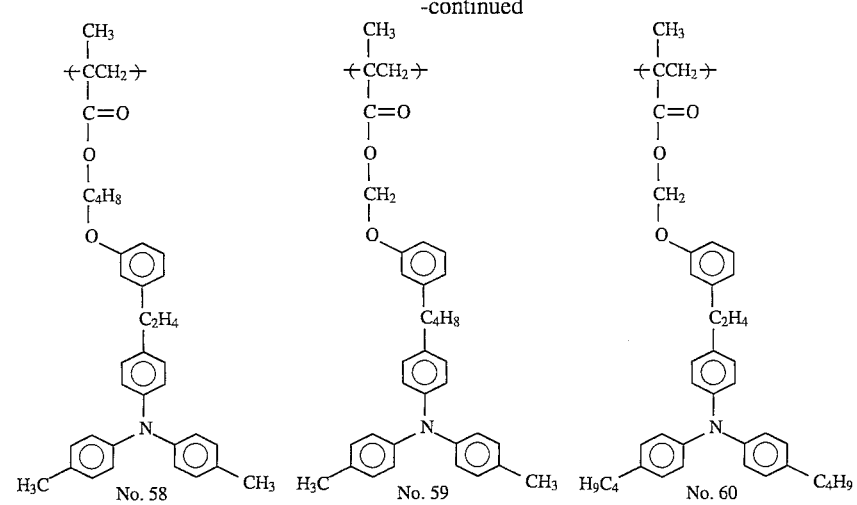
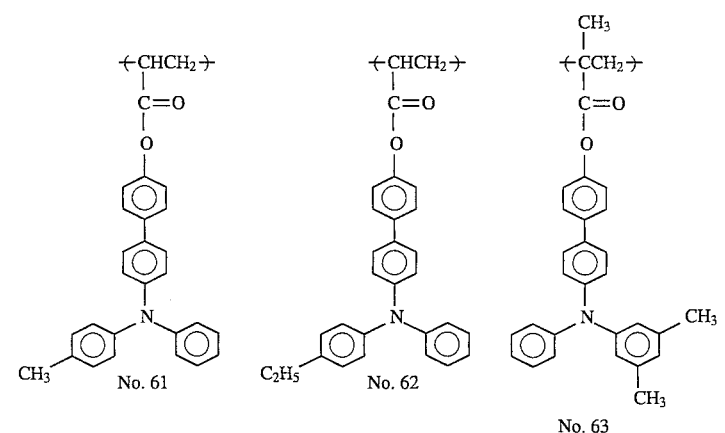
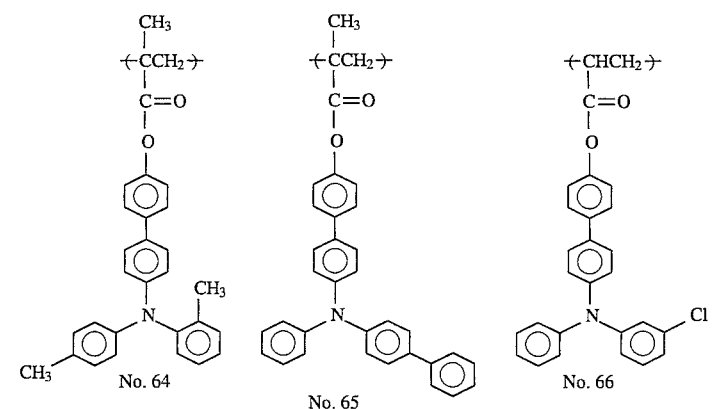

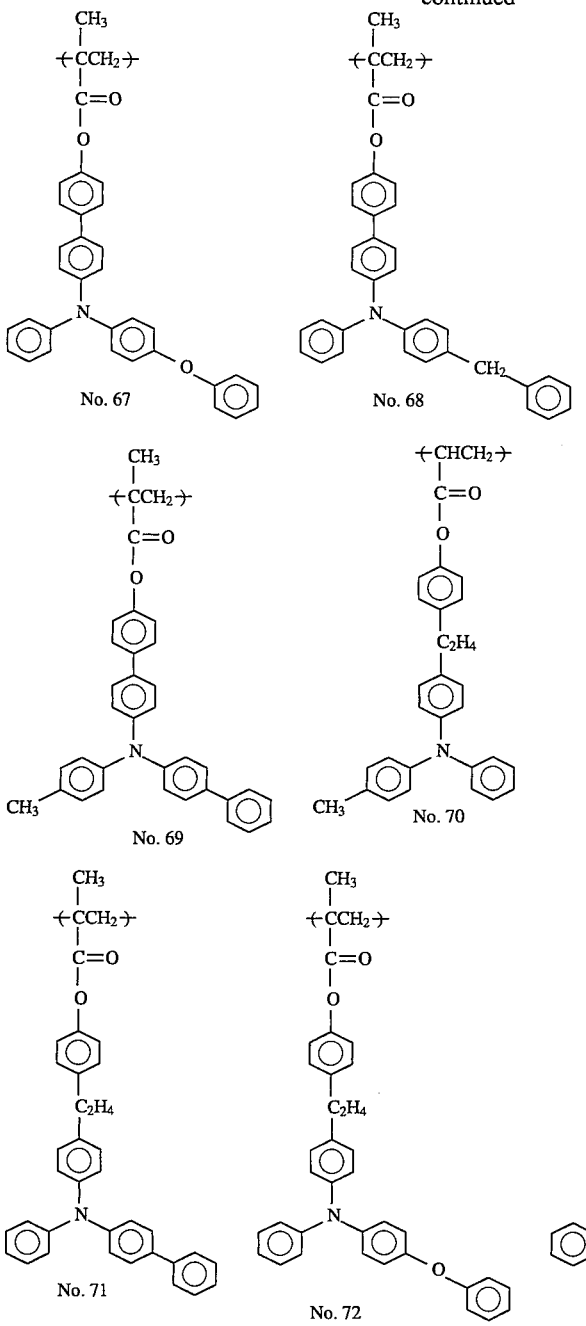

The above polymers serve so effectively as charge transporting materials that satisfactory electric characteristics such as low residual potential, high photosensitivity and good film properties can be obtained when the charge transport layer of the photoconductor comprises these polymers. Furthermore, by dissolving only the above-mentioned polymer is a solvent such as toluene and coating the thus obtained coating liquid on a charge generation layer, the charge transport layer which essentially consists of the polymer according to the present invention can be formed on the charge generation layer.

It is reported by Stolka et al. that a film composed of a polymethyl methacrylate substituted by triphenylamine is fragile. However, in the polymer of the present invention, the distance between the vinyl chain of the acrylic group and the triphenylamine group is kept apart by a group such as $(C_nH_{2n}O)$, a phenyl group, and $(C_nH_{2n})$. Furthermore, the problem of the fragility of the film can be solved by selecting the substituted position of the acrylic group. Moreover, the film properties can be controlled by copolymerizing the acrylic acid ester of the present invention with other monomers.

Any monomers having an unsaturated double bond can be used as monomers which can be copolymerized with the acrylic acid ester moiety of formula (I). As such monomers, acrylic monomers and styrene monomers are preferred.

Examples of such an acrylic monomer are methyl acrylate, methyl methacrylate, ethyl acrylate, ethyl metharylate, n-butyl acrylate, n-butyl methacrylate, isobutyl acrylate, isobutyl methacrylate, propyl acrylate, propyl methacrylate, hexyl acrylate, hexyl methacrylate, cyclohexyl acrylate, cyclohexyl methacrylate, benzyl acrylate, benzyl methacrylate, 2,2,2-trifluoroethyl methacrylate, octafluoropentyl methacrylate, heptadecafluoro methacrylate, phenyl methacrylate, methoxyethyl methacrylate, ethoxyethyl methacrylate, 2-hydroxyethyl acrylate, 2-hydroxyethyl methacrylate, 2-hydroxypropyl acrylate, 2-hydroxypropyl methacrylate, 3-hydroxypropyl acrylate, and 3-hydroxypropyl methacrylate.

The above monomers can be used alone or in combination. The kinds of monomers to be copolymerized with the acrylic acid ester of the present invention, and the ratios of monomers for use in the polymerization are determined depending on the hardness, frictional coefficient, surface energy, and other properties including ozone resistance, light-resistance, humidity resistance, and electric properties of the polymer to be obtained, and with the film properties of the polymer including flexibility, adhesion properties, and compatibility (clarity), and the mechanical strength such as wear resistance, taken into consideration.

It is preferable that the acrylic acid ester moiety of formula (I) be contained in the polymer in the range of 30 wt. % to 90 wt. %. When the ratio of the acrylic acid ester moiety as repeat unit contained in the polymer is within the above range, the obtained photoconductor has sufficient photosensitivity, and the film properties such as adhesion properties and flexibility of the charge transport layer of the obtained photoconductor do not deteriorate.

As a method of polymerization, solution polymerization using a radical, emulsion polymerization, suspension polymerization for obtaining a bead-type polymer, and ion polymerization using ions such as anion and cation are usable.

In the case where the monomer which comprises a hydroxyl-group-including repeat unit is employed for the polymerization with the acrylic acid ester moiety of formula (I), the mechanical strength of the film can be further improved by crosslinking with an isocyanate compound. In this case, it is preferable that the ratio of the hydroxyl-group-containing monomer be 5 to 20 wt. %. When the amount of the above monomer is within the above range, the adhesion properties of the film do not deteriorate and the effect of improving the film hardness can be maintained. In addition, the photosensitivity of the obtained photoconductor is satisfactory.

As the above-mentioned isocyanate compound, polyisocyanate of formula (III) can preferably be used:

$$R^5[(R^6)_{n'}(NCO)_{n''}] \quad (III)$$

wherein $R^5$ represents an alkyl group having 3 to 20 carbon atoms, an alkoxyl group having 3 to 20 carbon atoms, an aryl group, or an aralkyl group; $R^6$ represents an alkyl group having 3 to 20 carbon atoms, an alkoxyl group having 3 to 20 carbon atoms, an aryl group, or an aralkyl group, which can be attached to $R^5$ directly or through —NHCO—; n' is an integer of 0 to 3; and n" is 2 or 3.

Specific examples of the isocyanate compound for use in the polymerization are toluylene diisocyanate, 3,3'-dimethyl- 1-diphenyl-4,4'-diisocyanate, diphenylmethane-4,4'-diisocyanate, and triphenylmethane triisocyanate.

As commercially available isocyanate compounds, polyisocyanate compounds such as "Sumidur L", "Sumidur HL", "Sumidur VL", and "Sumidur N" (Trademark), made by Sumitomo Bayer Urethane Co., Ltd., and crosslinking isocyanate compounds such as "Takenate 500" (Trademark), made by Takeda Chemical Industries, Ltd., and "Burnock D-750" (Trademark), made by Dainippon Ink & Chemicals, Incorporated can be employed.

In the present invention, it is preferable that the amount of the isocyanate compound be equivalent to that of the hydroxyl group in the polymer. However, the amount of the isocyanate compound may be more than or less than the amount of the hydroxyl group. Generally, 0.05 to 2 parts by weight of the isocyanate compound are employed to 10 parts by weight of the polymer. The isocyanate compound and the polymer are dissolved in an aromatic-type solvent such as toluene or a ketone-type solvent such as methyl ethyl ketone to prepare a coating liquid for a charge transport layer. The thus obtained liquid is coated on a charge generation layer, dried at 90° to 150° C., and cured, so that the charge transport layer is formed on the charge generation layer.

With respect to the structure, the photoconductors can be roughly classified into a group of a negatively-chargeable photoconductor comprising a substrate and a charge generation layer and a charge transport layer which are successively overlaid on the substrate; a group of a positively-chargeable photoconductor comprising a substrate and a charge transport layer and a charge generation layer which are successively overlaid on the substrate; and a group of a positively-chargeable photoconductor comprising a substrate and a single photoconductive layer formed thereon. The polymer comprising the acrylic acid ester moiety as repeat unit according to the present invention can be used in any of the above-mentioned photoconductors.

Specific examples of the charge generating material for use in the photoconductors are as follows: a condensed polycyclic quinone compound such as Vat Orange 3 (C.I. No. 59300); a perylene compound (C.I. No. 38001); an azo pigment having a carbazole skeleton (Japanese Laid-Open Patent Application 53-95033); an azo pigment having a styryl stilbene skeleton (Japanese Laid-Open Patent Application 53-138229); an azo pigment having a triphenylamine skeleton (Japanese Laid-Open Patent Application 53-132547), an azo pigment having a dibenzothiophene skeleton (Japanese Laid-Open Patent Application 54-21728); an azo pigment having an oxidiazole skeleton (Japanese Laid-Open Patent Application 54-12742); an azo pigment having a fluorenone skeleton (Japanese Laid-Open Patent Application 54-22834); an azo pigment having a bisstilbene skeleton (Japanese Laid-Open Patent Application 54-17733); an azo pigment having a distyryl oxadiazole skeleton (Japanese Laid-Open Patent Application 54-2129); an azo pigment having a distyryl carbazole skeleton (Japanese Laid-Open Patent Application 54-17734); a triazo pigment having a carbazole skeleton (Japanese Laid-Open Patent Application 57-195767); an azo pigment having an anthraquinone skeleton (Japanese Laid-Open Patent Application 57-202545); a metal or metal-free phthalocyanine; and a squarylium dye.

These charge generating materials may be used alone or in combination with a binder resin by pulverizing and dispersing in a solvent by a ball mill, attritor, or an oscillating mill.

Examples of the above-mentioned solvent are alcohols such as methanol and isopropyl alcohol; ketones such as acetone, methyl ethyl ketone, and cyclohexanone; ethers such as tetrahydrofuran, dioxane, and ethylene glycol dialkyl ether; esters such as ethyl acetate and butyl acetate; halogenated hydrocarbons such as methylene chloride, dichloroethane, and chlorobenzene; and aromatic hydrocarbons such as benzene, toluene, and xylene. In addition, the above solvents may be used in combination.

As the binder resin, polyvinyl butyral, polyvinyl acetal, cellulose derivatives, phenolic rein, epoxy resin, acrylic resin, polyester, silicone resin, and polyvinyl acetate can be employed.

It is preferable that the pigment be pulverized and dispersed so as to have an average particle diameter of 0.3 μm or less.

As a method of forming the charge generation layer, conventional methods such as dip coating, spray coating, and roll coating can be employed. It is preferable that the thickness of the charge generation layer be 0.05 to 5 μm, more preferably 0.05 to 1 μm.

When the bladder resin is not contained in the dispersion for the charge generation layer, it is preferable to provide an intermediate layer in order to prevent the charge injection from the electroconductive substrate. As a binder resin used as a material for the intermediate layer, polyamide, polyacrylanilide, casein, vinyl chloride - vinyl acetate - maleic acid copolymer, and phenolic resin can be employed.

To form a charge transport layer, the polymer comprising the acrylic acid ester moiety as repeat unit according to the present invention is dissolved in an aromatic hydrocarbon such as toluene; a halogenated hydrocarbon such as methylene chloride; or a cyclic ether such as tetrahydrofuran to obtain a coating liquid for the charge transport layer. The thus obtained liquid is, for example, coated on the charge generation layer by dip coating, spray coating, or roll coating so as to have a thickness of 10 to 50 μm.

The polymer of the present invention can be used with a binder resin with good film properties such as polystyrene, styrene - methyl methacrylate copolymer, styrene - butadiene copolymer, hydrogenated styrene - butadiene copolymer, polymethyl methacrylate, polyester, polycarbonate, polyarylate, polysulfone, and polyphenylene oxide. It is preferable that the mixing ratio by weight of the binder resin to the polymer of the present invention be 2:10 to 10:10.

In the present invention, a conventionally used low-molecular-weight charge transporting material can be used with the polymer of the present invention in the charge transport layer of the photoconductor. As such a low-molecular-weight charge transporting material, pyrazoline compounds, α-phenylstilbene compounds, hydrazone compounds, diarylmethane compounds, triphenylamine compounds, divinylbenzene compounds, oxadiazole compounds, and diaminocarbazole compounds can be employed.

Other features of this invention will become apparent in the course of the following description of exemplary embodiments, which are given for illustration of the invention and are not intended to be limiting thereof.

SYNTHESIS EXAMPLE 1-1

Synthesis of 4-diphenylamino-4'-methoxystilbene

A mixture of 54.6 g (0.2 mol) of 4-diphenylaminobenzaldehyde, 51.6 g (0.2 mol) of diethyl-4-methoxybenzyl phosphonate, and 250 ml of dimethylformamide was placed in a 500 ml four-neck flask. 57.9 g of 28% sodium methylate was added dropwise to the above mixture with stirring at room temperature over a period of 15 minutes. Thus, the reaction was carried out at 50° to 60° C. for five hours. The thus obtained reaction mixture was diluted with 500 ml of water, and then made acid with the addition of acetic acid. Then the mixture was filtrated to obtain a wet cake. The thus obtained wet cake was washed with 100 ml of methanol three times, and recrystallized from a mixed solvent of ethanol and dioxane, whereby 46.2 g of 4-diphenylamino-4'-methoxystilbene was obtained as yellow crystals in the form of needles in a yield of 61.3%. The melting point of the obtained compound was 170° to 171.5° C.

FIG. 1 shows an IR spectrum of 4-diphenylamino-4'-methoxystilbene.

SYNTHESIS EXAMPLE 1-2

Synthesis of 1-(4-diphenylaminophenyl)-2-(4-methoxyphenyl)ethane 37.7 g (0.1 mol) of the 4-diphenylamino-4'-methoxystilbene prepared in Synthesis Example 1-1 was dissolved in 250 ml of dioxane. To the thus obtained mixture, 4 g of 5% Pd/C powder and then 2.4 l of hydrogen were added. A solvent was distilled away from the reaction mixture, whereby 1-(4-diphenylaminophenyl)-2-(4-methoxyphenyl)ethane was obtained as an oily transport compound of light yellow in color.

An IR spectrum of the thus obtained captioned compound indicates the disappearance of the characteristic absorption peaks of —HC=CH— at δ: 900 to 1000 cm$^{-1}$.

SYNTHESIS EXAMPLE 1-3

Synthesis of 1-(4-diphenylaminophenyl)-2-(4-hydroxyphenyl)ethane

A mixture of 38.5 g of the 1-(4-diphenylaminophenyl)-2-(4-methoxyphenyl)ethane prepared in Synthesis Example 1-2, 200 ml of sulfolane, and 45 g of sodium iodide was stirred in a four-neck flask at 120° C. to obtain a solution. The thus obtained solution was cooled to 60° C., and 2 ml of distilled water was added to the solution. 32.6 g of trimethylchlorosilane was then added dropwise to the above solution over a period of 30 minutes. Thus, the reaction was carried out at 60° to 70° C. for three hours. The thus obtained reaction mixture was poured into 500 ml of water, whereby a brown tar was obtained. The thus obtained tar was washed with 200 ml of water several times, and dissolved in 300 ml of toluene, whereby a brown toluene solution was obtained. The thus obtained toluene solution was washed twice with 100 ml of a saturated aqueous solution of sodium sulfite, whereby a transparent toluene solution of light yellow in color was obtained. After the thus obtained transparent toluene solution was dried over anhydrous magnesium sulfate, a solvent was distilled away. The thus obtained product was subjected to chromatography using a silica gel and toluene, whereby 31.4 g of 1-(4-diphenylaminophenyl)-2-(4-hydroxyphenyl)ethane was obtained as an oily material.

Figure 2:
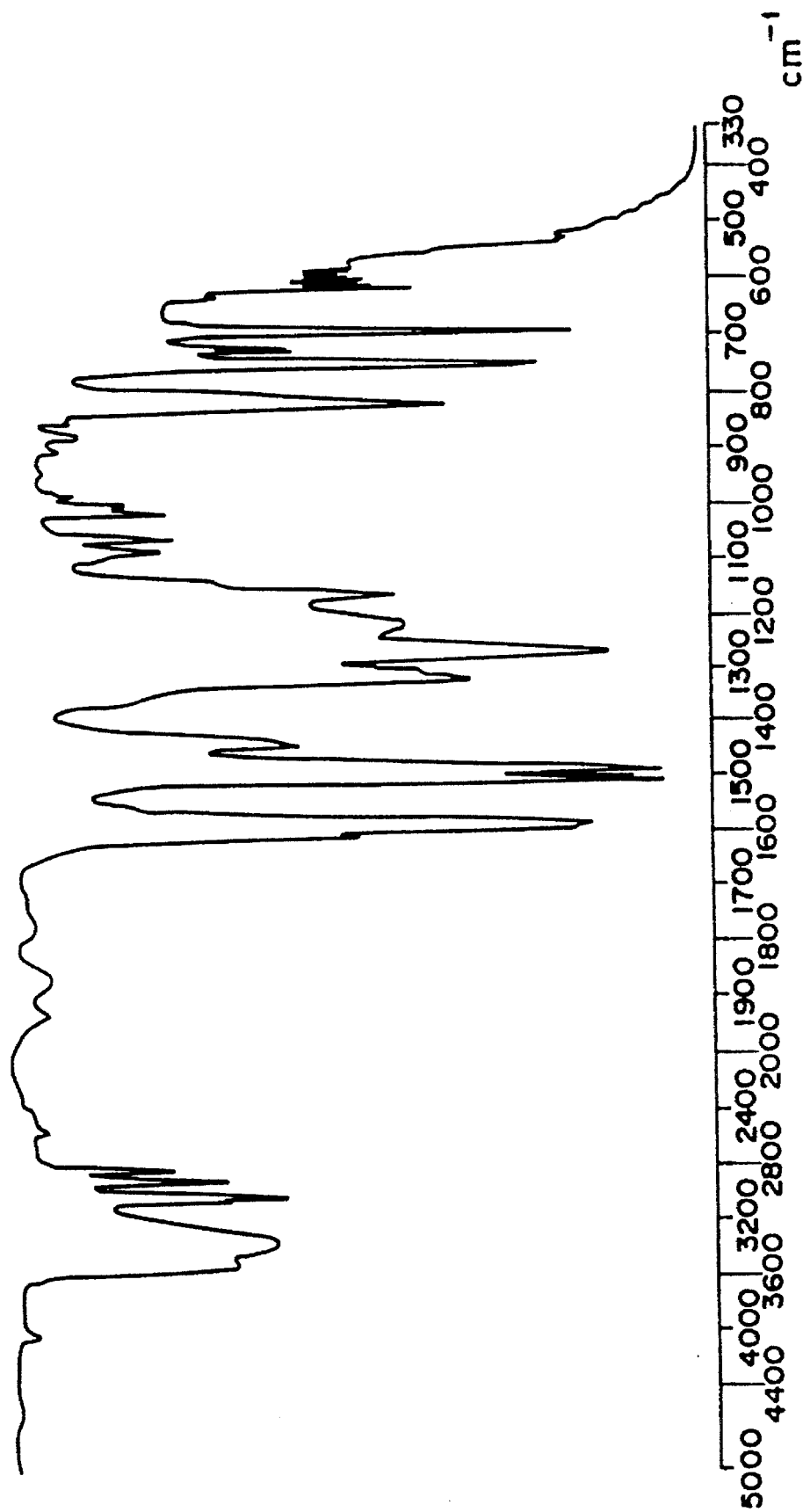
FIG. 2 is an IR spectrum of 1-(4-diphenylaminophenyl)-2-(4-hydroxyphenyl)ethane.

FIG. 2 shows an IR spectrum of 1-(4-diphenylaminophenyl)- 2-(4-hydroxyphenyl)ethane.

The IR spectrum of the thus obtained compound indicates the characteristic absorption peaks of ν: OH at 3550 cm$^{-1}$ and 3400 cm$^{-1}$.

SYNTHESIS EXAMPLE 1-4

Synthesis of 4-[2'-(4"-diphenylaminophenyl)ethyl]phenyl methacrylate

A mixture of 31.4 g of the 1-(4-diphenylaminophenyl)-2-(4-hydroxyphenyl)ethane prepared in Synthesis Example 1-3, 150 ml of dioxane, 20 g of a 20% aqueous solution of sodium hydroxide was cooled at 5° C. 10.8 g of methacryl chloride was added dropwise to the above mixture, with stirring, with the temperature thereof being maintained at 10° C. or less. After the completion of dropwise addition of methacryl chloride, the reaction was carried out at room temperature for two hours. The thus obtained reaction mixture was poured into 500 ml of water, and then extracted with 300 ml of toluene. The thus extracted layer was washed twice with 200 ml of water, and dried over anhydrous magnesium sulfate. A solvent was distilled away, and then the obtained product was subjected to chromatography using a silica gel and toluene, whereby 30 g of a monomer of 4-[2'-(4"-diphenylaminophenyl)ethyl] phenyl methacrylate was obtained. The melting point of the obtained monomer was 105.5° to 107° C.

Figure 3:
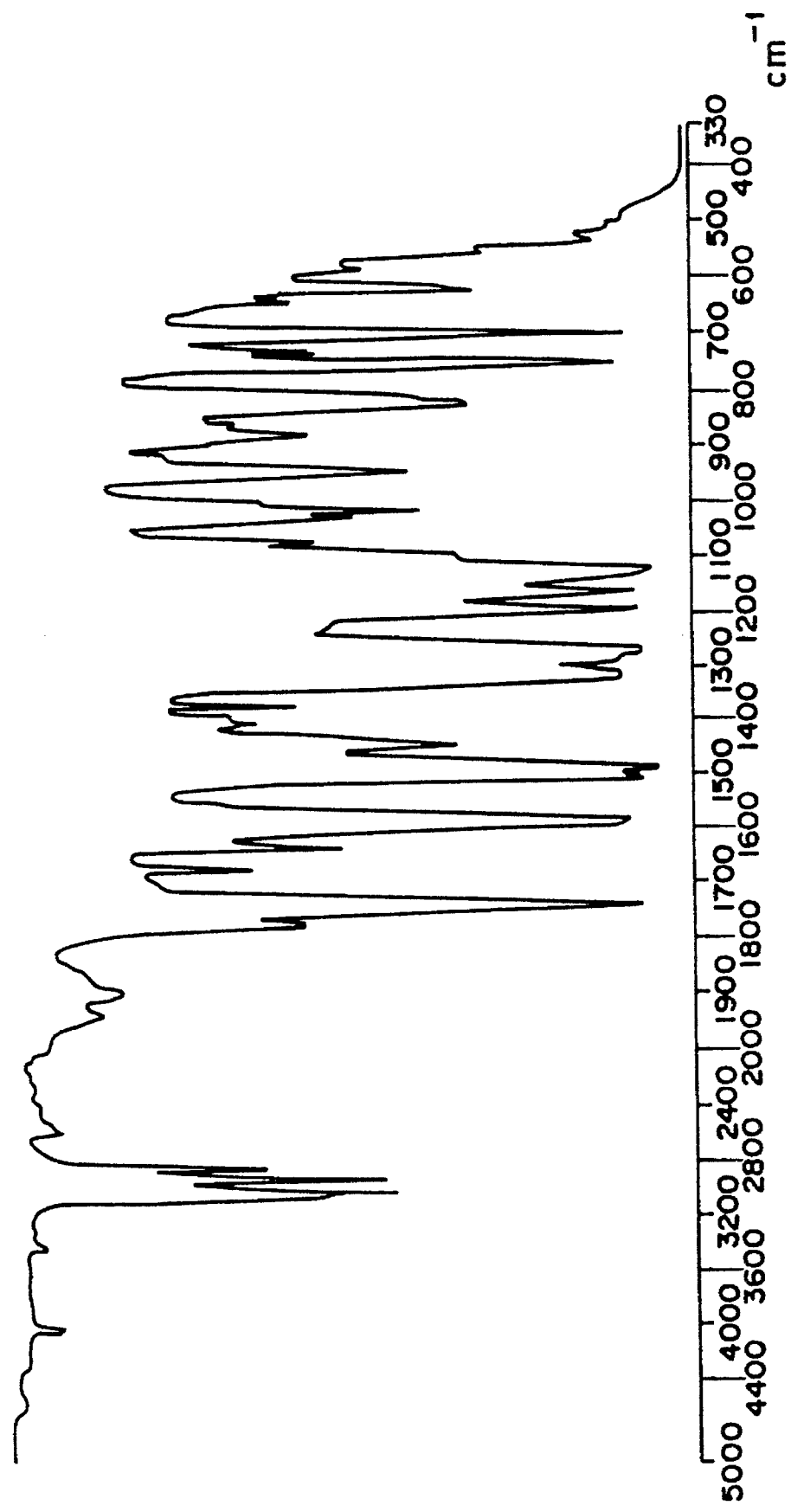
FIG. 3 is an IR spectrum of 4-[2'-(4''-diphenylaminophenyl)ethyl] phenyl methacrylate.

FIG. 3 shows an IR spectrum of 4-[2'-(4"-diphenylaminophenyl)ethyl] phenyl methacrylate.

The IR spectrum indicates the disappearance of the characteristic absorption peaks of v: OH at 3550 cm$^{-1}$ and 3400 cm$^{-1}$, and the appearance of the characteristic absorption peak of C=O at 1740 cm$^{-1}$ and the characteristic peak of =CH$_2$ at 950 cm$^{-1}$.

SYNTHESIS EXAMPLE 2-1

Synthesis of
1-(4-diphenylaminophenyl)-2-(4'-3"-hydroxypropoxyphenyl)ethane

A mixture of 36.5 g of the 1-(4-diphenylaminophenyl)-2-(4-hydroxyphenyl)ethane prepared in Synthesis Example 1-3, 24 g of a 20% aqueous solution of sodium hydroxide, and 200 ml of dioxide was heated to 50° C. and stirred. 11.1 g of epichlorohydrin was added dropwise to the above mixture with stirring over a period of 30 minutes. After the reaction was carried out at 60° C. for five hours, the thus obtained reaction mixture was poured into 500 ml of water. An oil layer was extracted with toluene, washed twice with 200 ml of water, dried over anhydrous magnesium sulfate, and subjected to column chromatography using a silica gel and toluene used as a developing solvent, whereby 20 g of 1-(4-diphenylaminophenyl)- 2-(4'-3"-hydroxypropoxyphenyl)ethane was obtained as an anhydrous oily product in a yield of 47.28%.

SYNTHESIS EXAMPLE 2-2

Synthesis of
γ-{4-[2-(4-diphenylaminophenyl)ethyl]} phenyloxypropyl methacrylate 20 g of the alcohol precursor prepared in Synthesis Example 2-1 was dissolved in 150 ml of dioxane to obtain a solution. With addition of 4 ml of pyridine, the thus obtained mixture was cooled to 5° C. 5.9 g of methacryl chloride was added dropwise to the above mixture with stirring. After the completion of dropwise addition of methacryl chloride, the reaction was carried out for two hours. The thus obtained reaction mixture was poured into 300 ml of water and extracted with 200 ml of toluene. The extract layer was washed twice with 200 ml of water, dried over anhydrous magnesium sulfate, and subjected to column chromatography using silica gel and toluene, whereby 19 g of γ-{4-[2-(4-diphenylaminophenyl)ethyl]}phenyloxypropyl methacrylate was obtained as a colorless oily monomer in a yield of 82.0%.

SYNTHESIS EXAMPLE 3

Synthesis of
poly-4-[2'-(4"-diphenylaminophenyl)ethyl] phenyl methacrylate (Polymer No. 26)

A mixture of 25 g of the 4-[2'-(4"-diphenylaminophenyl)ethyl] phenyl methacrylate prepared in Synthesis Example 1-4, 50 g of toluene, and 0.09 g of azobisisobutylnitrile was stirred at room temperature in a stream of nitrogen for one hour. Then the polymerization reaction was carried out at 60° C. for five hours, 70° C. for two hours, 80° C. for two hours, and 100° C. for one hour. The thus obtained reaction mixture was added dropwise to 2 l of methanol, so that a polymer separated out. After the thus obtained polymer was washed with 500 ml of acetone, the polymer was dissolved in 300 ml of toluene and the polymer was reprecipitated several times using 2 l of methanol, whereby 18 g of the captioned compound was obtained in a yield of 72%.

Figure 4:
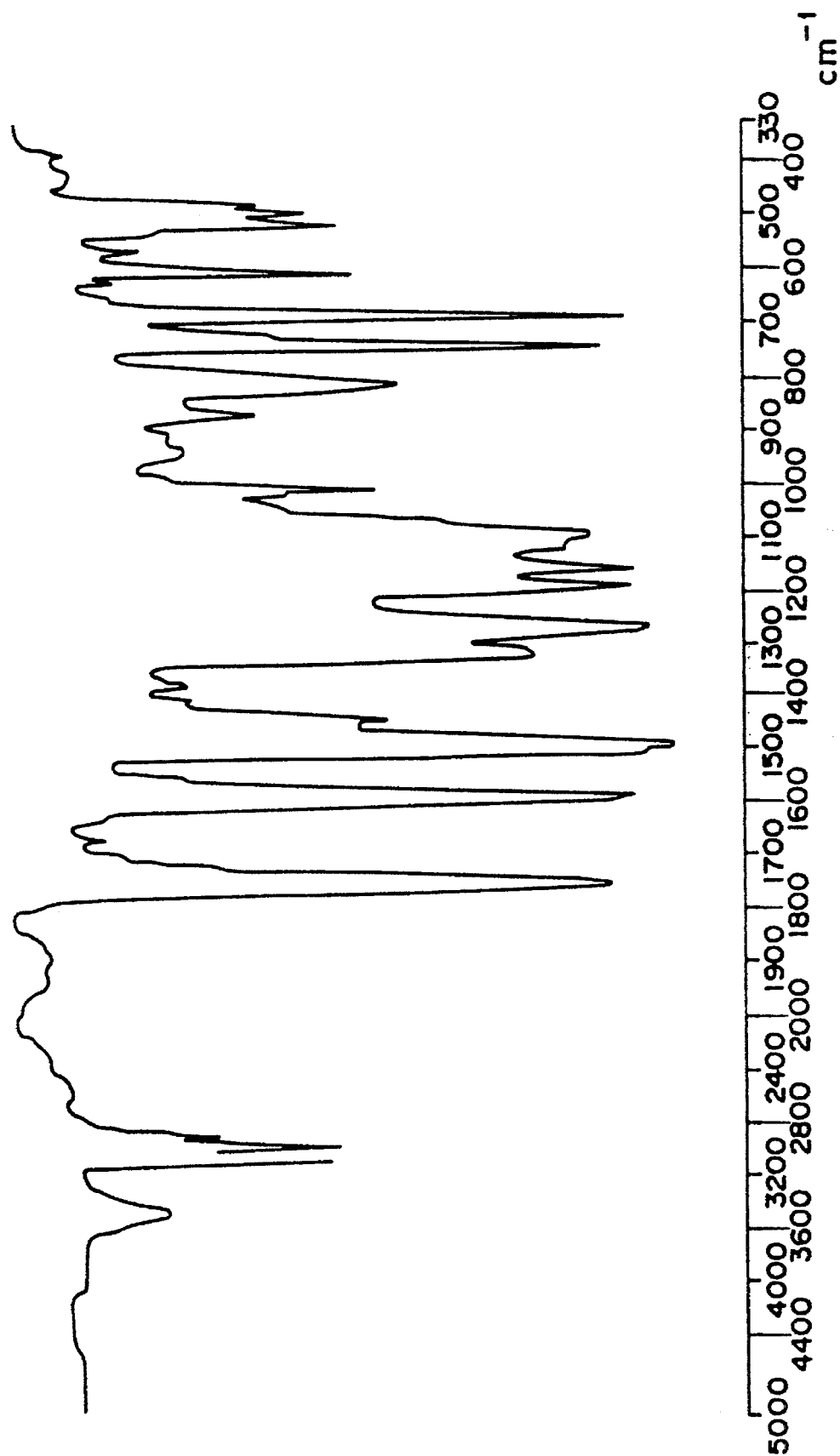
FIG. 4 is an IR spectrum of poly-4-[2'-(4''-diphenylaminophenyl)ethyl] phenyl methacrylate.

FIG. 4 shows an IR spectrum of poly-4-[2'-(4"-diphenylaminophenyl)ethyl] phenyl methacrylate.

SYNTHESIS EXAMPLE 4

Synthesis of
poly-γ-{4-[2-(4-diphenylaminophenyl)ethyl]}phenyloxypropyl methacrylate (Polymer No. 43)

The procedure for preparing the poly-4-[2'-(4"-diphenylaminophenyl)ethyl] phenyl methacrylate in Synthesis Example 3 was repeated except that the 4-[2'-(4"-diphenylaminophenyl)ethyl] phenyl methacrylate prepared in Synthesis Example 1-4 used in Synthesis Example 3 was replaced by γ-{ 4-[2-(4-diphenylaminophenyl)ethyl]}phenyloxypropyl methacrylate prepared in Synthesis Example 2-2, whereby the captioned polymer was obtained. From the result of gas permeation chromatography, the molecular weight of the obtained polymer was 5,000 to 100,000. It can be considered that a difference in the molecular weight was caused by a slight difference in steric hindrance of the monomers, electron density of the vinyl groups, and the reaction atmosphere. The difference in the molecular weight does not largely affect on the electric properties, but substituents and the position of the substituents largely affect on the electric properties.

SYNTHESIS EXAMPLE 5

A mixture of 20 g of a monomer of Polymer No. 3, 7 g of n-butylmethacrylate (nBMA), 0.09 g of azobisisobutylnitrile (AIBN), and 63 g of toluene was placed in a four-neck flask. After a nitrogen gas was bubbled through the mixture at room temperature over a period of one hour, the reaction was carried out at 60° C. for five hours, 70° C. for two hours, and 80° C. for four hours. The thus obtained reaction mixture was a light brown viscous liquid. This reaction mixture was diluted with 200 ml of toluene, and added dropwise to 2 l of methanol, so that a product separated out. This product was washed with 500 ml of acetone, dissolved in 200 ml of toluene, and reprecipitated with methanol, whereby a polymer of the present invention was obtained.

SYNTHESIS EXAMPLE 6

The procedure for preparing the polymer in Synthesis Example 5 was repeated except that the mixture of 20 g of the monomer of Polymer No. 3, 7 g of n-butylmethacrylate (nBMA), 0.09 g of azobisisobutylnitrile (AIBN), and 63 g of toluene used in Synthesis Example 5 was replaced by a mixture of 20 g of a monomer of Polymer No. 19, 5 g of methyl methacrylate (MMA), 5 g of nBMA, 0.1 g of AIBN, and 70 g of toluene, whereby a polymer of the present invention was obtained.

SYNTHESIS EXAMPLE 7

The procedure for preparing the polymer in Synthesis Example 5 was repeated except that the mixture of 20 g of the monomer of Polymer No. 3, 7 g of n-butylmethacrylate (nBMA), 0.09 g of azobisisobutylnitrile (AIBN), and 63 g of toluene used in Synthesis Example 5 was replaced by a mixture of 20 g of a monomer of Polymer No. 27, 5 g of nBMA, 2 g of MMA, 3 g of 2-hydroxyethyl methacrylate (2HEMA), 0.1 g of AIBN, and 70 g of toluene, whereby a light brown viscous liquid with a 30% solid content was obtained.

SYNTHESIS EXAMPLE 8

The procedure for preparing the polymer in Synthesis Example 5 was repeated except that the mixture of 20 g of the monomer of Polymer No. 3, 7 g of n-butylmethacrylate (nBMA), 0.09 g of azobisisobutylnitrile (AIBN), and 63 g of toluene used in Synthesis Example 5 was replaced by a mixture of 20 g of a monomer of Polymer No. 35, 5 g of 2-ethylhexyl methacrylate (2EHMA), 4 g of benzyl methacrylate (BzyMA), 4 g of 2-hydroxypropyl methacrylate, 0.12 g of AIBN, and 77 g of toluene, whereby a light brown viscous liquid with a 30% solid content was obtained.

Each of the polymers obtained in Synthesis Examples 7 and 8 was employed as a coating liquid for a charge transport layer without carrying out the reprecipitation of the polymer.

EXAMPLE 1

Formation of Intermediate Layer 4 parts by weight of a polyamide resin (Trademark "CM-8000", made by Toray Industries, Inc.), 60 parts by weight of methanol, and 36 parts by weight of butanol were mixed to prepare a coating liquid for an intermediate layer. The thus prepared liquid was coated by a doctor blade on an aluminum plate with a thickness of 0.3 mm serving as a substrate and dried at 120° C., so that an intermediate layer with a thickness of 0.3 μm was formed on the substrate.

Formation of Charge Generation Layer

A mixture of 22 parts by weight of a compound of formula (IV) and 440 parts by weight of cyclohexanone was pulverized and dispersed in a ball mill for 72 hours.

600 parts by weight of cyclohexanone was further added to the above prepared mixture and dispersed in the ball mill for 3 hours. The thus obtained dispersion was diluted with 800 parts by weight of a mixed solvent of cyclohexanone and methyl ethyl ketone at a mixing ratio by weight of 1:1 to prepare a coating liquid for a charge generation layer.

The thus prepared liquid was coated on the above prepared intermediate layer by a doctor blade, and dried at 120° C. for 10 minutes, so that a charge generation layer with a thickness of 0.3 μm was formed on the intermediate layer.

Formation of Charge Transport Layer 5 parts by weight of Polymer No. 1 (Mn=23,000) and 5 parts by weight of toluene were mixed to prepare a coating liquid for a charge transport layer. The thus prepared liquid was coated on the above prepared charge generation layer by a doctor blade, and dried at 120° C. for 20 minutes, so that a charge transport layer with a thickness of 23 μm was formed n the charge generation layer.

Thus, an electrophotographic photoconductor No. 1 of the present invention was obtained.

EXAMPLES 2 to 14

The procedure for preparing the electrophotographic photoconductor in Example 1 was repeated except that the Polymer No. 1 for use in the coating liquid for the charge transport layer n Example 1 was replaced by each of the Polymers shown in Table 1, whereby electrophotographic photoconductors Nos. 2 to 14 of the present invention were obtained.

Each of the thus prepared electrophotographic photoconductors No. 1 to No. 14 according to the present invention was subjected to the electrophotographic property evaluation test using a commercially available electrostatic copying sheet testing apparatus ("Paper Analyzer Model SP-428" made by Kawaguchi Electro Works Co., Ltd.) in the dynamic mode.

Each photoconductor was charged under application of −6 kV of corona charge for 20 seconds, and the surface potential Vm (volt) of the photoconductor was measured. Then, each electrophotographed photoconductor was allowed to stand in the dark for 20 seconds without applying any charge thereto, and the surface potential Vo (volt) of the photoconductor was measured. Each photoconductor was then illuminated by a tungsten lamp in such a manner that the illuminance on the surface of the photoconductor was 4.5 lux, and the exposure $E_{1/2}$ (lux·sec) and $E_{1/10}$ (lux·sec) required to reduce the initial surface potential Vo to respectively ½ and ⅟₁₀ thereof were measured. The surface potential Vr (volt) of the photoconductor 30 seconds after the

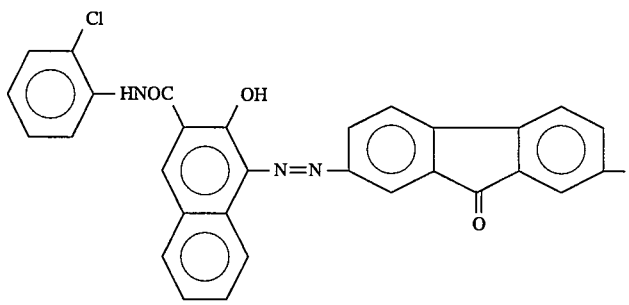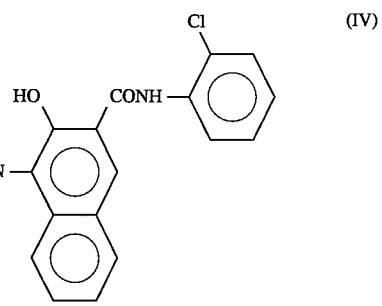

(IV)

application of tungsten white light was also measured. The results are shown in Table 1.

TABLE 1

| Example No. | Polymer No. | Vm (v) | Vo (v) | $E_{1/2}$ (lux · sec) | $E_{1/10}$ (lux · sec) | Vr (v) |
|---|---|---|---|---|---|---|
| Ex. 1 | 1 | 1200 | 900 | 1.10 | 2.23 | 0 |
| Ex. 2 | 2 | 1340 | 1280 | 1.89 | 3.92 | 0 |
| Ex. 3 | 3 | 1140 | 890 | 1.01 | 2.12 | 0 |
| Ex. 4 | 4 | 1240 | 860 | 1.21 | 2.53 | 0 |
| Ex. 5 | 11 | 1180 | 820 | 1.05 | 2.26 | 0 |
| Ex. 6 | 14 | 1200 | 1040 | 1.20 | 2.58 | 0 |
| Ex. 7 | 26 | 1420 | 1240 | 2.23 | 4.56 | 0 |
| Ex. 8 | 27 | 1320 | 1080 | 1.73 | 3.51 | 0 |
| Ex. 9 | 34 | 1480 | 1230 | 2.05 | 4.19 | 0 |
| Ex. 10 | 35 | 1280 | 910 | 1.46 | 2.81 | 0 |
| Ex. 11 | 36 | 1180 | 890 | 1.37 | 2.77 | 0 |
| Ex. 12 | 42 | 1160 | 870 | 1.29 | 2.57 | 0 |
| Ex. 13 | 51 | 1260 | 940 | 1.49 | 3.02 | 0 |
| Ex. 14 | 52 | 1160 | 870 | 1.18 | 2.25 | 0 |

EXAMPLES 15 TO 19

The procedure for preparing the electrophotographic photoconductor in Example 1 was repeated except that the Polymer No. 1 for use in the coating liquid for the charge transport layer in Example 1 was replaced by each of the copolymers shown in Table 2, whereby electrophotographic photoconductors Nos. 15 to 19 according to the present invention were obtained.

Each of the thus obtained electrophotographic photoconductors Nos. 15 to 19 was subjected to the evaluation test in the same manner as in Examples 1 to 14. The results are also shown in Table 2.

TABLE 2

| Example No. | Copolymer | Vm (v) | Vo (v) | $E_{1/2}$ (lux · sec) | $E_{1/10}$ (lux · sec) | Vr (v) |
|---|---|---|---|---|---|---|
| Ex. 15 | Copolymer prepared in Synthesis Ex. 5 | 1480 | 1230 | 3.46 | 7.86 | 3 |
| Ex. 16 | Copolymer prepared in Synthesis Ex. 6 | 1350 | 1180 | 3.06 | 7.21 | 3 |
| Ex. 17 | Polymer No. 7: nBMA: 2EHMA (20:5:5) | 1520 | 1310 | 4.84 | 9.78 | 7 |
| Ex. 18 | Polymer No. 27: nHMA(*): BzyMA (20:4:4) | 1550 | 1350 | 5.62 | 11.09 | 12 |
| Ex. 19 | Polymer No. 42: nHMA: cHMA(**) (20:2:2) | 1330 | 1100 | 3.24 | 7.87 | 12 |

*: nHMA is n-hexyl methacrylate
**: cHMA is cyclohexyl methacrylate

EXAMPLE 20

An intermediate layer and a charge generation layer were successively formed on a substrate in the same manner as in Example 1.

Formation of Charge Transport Layer 5 parts by weight of the copolymer prepared in Synthesis Example 5 (the same as used in Example 15) and 1 part by weight of a charge transporting material of formula (V) were dissolved in 10 parts by weight of toluene to prepare a coating liquid for a charge transport layer.

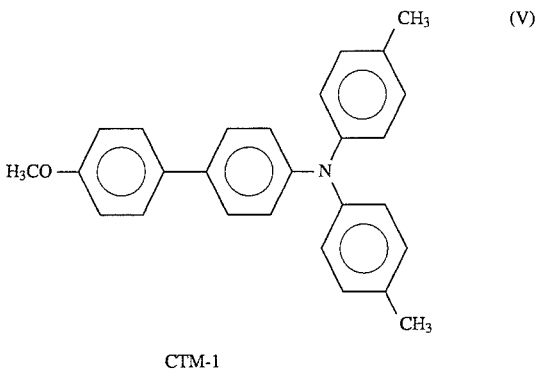

CTM-1

The thus prepared liquid was coated on the above prepared charge generation layer by a doctor blade, and dried at 120° C. for 20 minutes, so that a charge transport layer with a thickness of 23 μm was formed on the charge generation layer.

Thus, an electrophotographic photoconductor No. 20 of the present invention was obtained.

EXAMPLE 21

The procedure for preparing the electrophotographic photoconductor in Example 20 was repeated except that the copolymer prepared in Synthesis Example 5 for use in the coating liquid for the charge transport layer in Example 20 was replaced by the copolymer prepared in Synthesis Example 6 (the same as used in Example 16), whereby an electrophotographic photoconductor No. 21 of the present invention was obtained.

EXAMPLE 22

The procedure for preparing the electrophotographic photoconductor in Example 20 was repeated except that the copolymer prepared in Synthesis Example 5 and the charge transporting material of formula (V) for use in the coating liquid for the charge transport layer in Example 20 were respectively replaced by the copolymer used in Example 18 (shown in Table 2), and a charge transporting material of formula (VI), whereby an electrophotographic photoconductor No. 22 of the present invention was obtained.

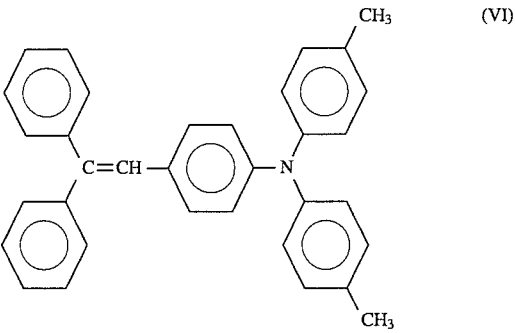

CTM-2

Each of the thus obtained electrophotographic photoconductors Nos. 20 to 22 was subjected to the evaluation test in the same manner as in Examples 1 to 14. The results are shown in Table 3.

TABLE 3

| Example No. | Vm (v) | Vo (v) | $E_{1/2}$ (lux · sec) | $E_{1/10}$ (lux · sec) | Vr (v) |
|---|---|---|---|---|---|
| Ex. 20 | 1220 | 1080 | 1.10 | 2.30 | 0 |
| Ex. 21 | 1240 | 1040 | 1.13 | 2.38 | 0 |
| Ex. 22 | 1340 | 1100 | 1.63 | 3.44 | 0 |

EXAMPLE 23

An intermediate layer and a charge generation layer were successively formed on a substrate in the same manner as in Example 1.

Formation of Charge Transport Layer 0.1 parts by weight of toluylenediisocyanate were added to 5 parts by weight of the copolymer prepared in Synthesis Example 7 to prepare a coating liquid for a charge transport layer. The thus obtained liquid was coated by a doctor blade on the above prepared charge generation layer, dried at 130° C. for 30 minutes, and cured, so that a charge transport layer was formed on the charge generation layer.

Thus, an electrophotographic photoconductor No. 23 of the present invention was obtained.

EXAMPLE 24

The procedure for preparing the electrophotographic photoconductor in Example 23 was repeated except that the copolymer prepared in Synthesis Example 7 for use in the coating liquid for the charge transport layer in Example 23 was replaced by the copolymer prepared in Synthesis Example 8, so that an electrophotographic photoconductor No. 24 of the present invention was obtained.

Each of the thus obtained electrophotographic photoconductors Nos. 23 and 24 was subjected to the evaluation test in the same manner as in Example 1 to 14. The results are shown in Table 4.

TABLE 4

| Example No. | Vm (v) | Vo (v) | $E_{1/2}$ (lux · sec) | $E_{1/10}$ (lux · sec) | Vr (v) |
|---|---|---|---|---|---|
| Ex. 23 | 1580 | 1330 | 4.75 | 10.08 | 25 |
| Ex. 24 | 1590 | 1350 | 5.13 | 13.45 | 38 |

When each of the thus obtained electrophotographic photoconductors Nos. 23 and 24 was dipped into an isoparaffin-type solvent such as "Isopar-H" (Trademark), made by Exxon Chemical Japan Ltd., toluene, or methyl ethyl ketone, the charge transport layer of the photoconductor was not dissolved with any of the above solvents.

In the present invention, the acrylic acid ester of formula (II) and the polymer comprising the acrylic acid ester moiety of formula (I) as repeat unit are novel. When the above-mentioned polymer is used as a charge transporting material in the electrophotographic photoconductor, high photosensitivity and durability can be imparted thereto.

What is claimed is:

1. An acrylic acid ester of the formula

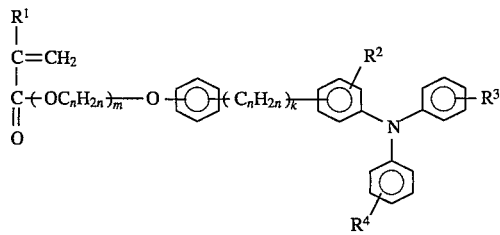

wherein $R^1$ represents hydrogen or a methyl group; $R^2$, $R^3$ and $R^4$ each represent hydrogen, an alkyl group having 1 to 4 carbon atoms, a benzyl group, a phenyl group or chlorine; n is an integer of 1 to 4; m is 0 or 1; and k is 0 or 1.

2. An acrylic acid ester according to claim 1, having the formula

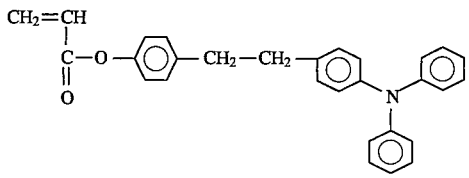

* * * * *

UNITED STATES PATENT AND TRADEMARK OFFICE
CERTIFICATE OF CORRECTION

PATENT NO. : 5,488,137

DATED : JANUARY 30, 1996

INVENTOR(S) : HIROSHI TAMURA ET AL

It is certified that error appears in the above-indentified patent and that said Letters Patent is hereby corrected as shown below:

Column 7, Figure 17, " 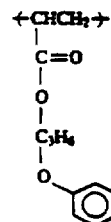 " should read -- 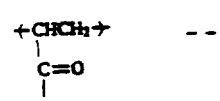 --

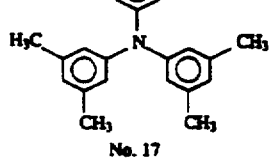 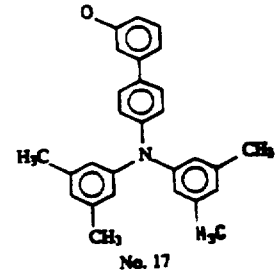

UNITED STATES PATENT AND TRADEMARK OFFICE
CERTIFICATE OF CORRECTION

PATENT NO. : 5,488,137
DATED : JANUARY 30, 1996
INVENTOR(S) : HIROSHI TAMURA ET AL

It is certified that error appears in the above-indentified patent and that said Letters Patent is hereby corrected as shown below:

Column 22, line 67, "rein" should read --resin--.

Column 23, line 11, "bladder" should read --binder--.

Column 24, line 16, "transport" should read --transparent--.

Signed and Sealed this

Twelfth Day of November, 1996

Attest:

BRUCE LEHMAN

Attesting Officer

Commissioner of Patents and Trademarks